United States Patent [19]
Ratton et al.

[11] Patent Number: 5,388,453
[45] Date of Patent: Feb. 14, 1995

[54] METHOD AND APPARATUS FOR MEASURING EVAPORATIVE VEHICLE EMISSIONS

[75] Inventors: Kenneth Ratton, Farmington Hills; James Juranitch, Walled Lake, both of Mich.

[73] Assignee: Power-Tek, Inc., Farmington Hills, Mich.

[21] Appl. No.: 23,322

[22] Filed: Feb. 26, 1993

[51] Int. Cl.⁶ ............................................. G01M 15/00
[52] U.S. Cl. .................................. 73/117.1; 73/23.31
[58] Field of Search .................... 73/23.31, 116, 117.1, 73/149, 865.6

[56] References Cited

U.S. PATENT DOCUMENTS

| | | | |
|---|---|---|---|
| 4,964,298 | 10/1990 | Matsushita | 73/117.1 |
| 5,167,146 | 12/1992 | Hostetter | 73/117.1 |
| 5,231,873 | 8/1993 | Lindberg | 73/149 |

*Primary Examiner*—Robert Raevis
*Attorney, Agent, or Firm*—Brooks & Kushman

[57] ABSTRACT

Provided is a method and apparatus for measuring evaporative vehicle emissions. In accordance with the invention, there is provided a leak-tolerant apparatus for use in cooperation with an absolute fluid pressure sensor for measuring evaporative emissions for motor vehicles in accordance with prescribed fluid-temperature profiles. The apparatus includes control means in electrical communication with fluid temperature sensor, a fluid pressure sensor and a volume compensation device for determining the quantity of fluid required to be provided to or evacuated from the volume compensation device in accordance with the ideal gas law. In operation, the control means compares the mass flow, volumetric flow, total mass or total volume with the rate or total change in temperature and pressure and corrects a flow metering device so as to allow more or less fluid into or out of the volume compensation device to achieve the desired test chamber volume compensation.

12 Claims, 9 Drawing Sheets

METHOD AND APPARATUS FOR MEASURING EVAPORATIVE VEHICLE EMISSIONS

TECHNICAL FIELD

This invention relates generally to Sealed Housings for Evaporative Determination. More specifically, this invention relates to a leak-tolerant control system and method for determining evaporative vehicle emissions.

BACKGROUND OF THE INVENTION

As used in the art, the acronym "SHED" generally refers to Sealed Housings For Evaporative Determination. These SHEDs are generally rectangular enclosures which define fluid-fillable test chambers adapted to measure evaporative emissions such as hydrocarbon (HC) from automobiles, trucks, and other motor vehicles. Historically, such testing was performed while the test chamber fluid (typically air) was maintained at a constant temperature. In operation, the test vehicle was placed in the SHED with the engine and all other equipment turned off. The door to the SHED was then closed and sealed. Thereafter, selected emissions such as hydrocarbon were measured at the beginning and end of a fixed time period which was generally one hour. The SHED test is one step of the Federal Test Procedure which is described in the Federal Register subpart B 86.101 to 86.145-82.

Those skilled in the art will recognize that recent proposed regulations developed for the Clean Air Act have revised the evaporative portion of the Federal Test Procedure. As revised, the evaporative portion now requires the use of a variable-volume/variable-temperature test chamber. As more thoroughly described in the Draft Evaporative Regulations OMB1 of Nov. 18, 1992, Sec. 86.078-3 to 86.098-10, new SHEDs must therefore define fluid-fillable test chambers capable of changing fluid temperature following prescribed temperature profiles.

It should be noted that sealing technology, which was not a significant issue under the prior art constant temperature systems, has now become a complex problem for SHED designers under the variable temperature requirements. As those skilled in the art will recognize, by design, conventional SHEDs must include a plurality of penetrations for sample ports and temperature probes as well as a vehicle entrance/exit door, an operator egress door and a purge vent. All of these doors and penetrations must be sufficiently sealed or leakage will occur and emission sample will be lost. Because of the new variable temperature requirements and the need for a sealed housing to prevent loss of emissions during the expansion portions of the test, the corresponding volume compensation requirement was introduced to avoid pressurizing the SHED.

To comply with the new volume compensation requirements, conventional SHEDs have incorporated various volume control devices for varying the volume of the fluid-fillable test chambers during expansion and contraction of test chamber fluid. Typically, such devices have been provided in fluid communication with the fluid (typically air) outside of the test chamber and are controlled by pure pressure feedback systems through the use of differential pressure transducers. Typical volume compensation devices include, for example, a plurality of inflatable bags which are disposed on the internal walls of the test chamber. During expansion of the test chamber fluid, the bags are deflated to increase the volume of the test chamber. Similarly, during contraction cycles, the bags are inflated to decrease the volume of the test chamber. It should be noted, however, that because these devices use differential pressure transducers as feedback, a near-perfect seal is required for the SHED to operate properly. Indeed, induced pressure variations, however slight, will bias the differential pressure transducer and cause an error in the amount of volume compensation. The resulting error will be magnified by forcing the sample out of the SHED or diluting the sample by drawing fluid into the SHED. Because truly "sealed" housings are nearly impossible to achieve, the pressure control systems of the prior art have proven unreliable and thus highly susceptible to error.

DISCLOSURE OF INVENTION

It is an object of the present invention to overcome the limitations of the prior art by providing a leak-tolerant method and apparatus for use in cooperation with an absolute fluid pressure sensor for measuring evaporative emissions from motor vehicles in accordance with prescribed fluid-temperature profiles.

In carrying out the above object, the apparatus of the present invention incorporates an open-loop control system which relies on the ideal expansion of test chamber fluid and thus obviates the need for either a differential transducer or a perfectly sealed housing. The control system is predictive in nature and thus automatically compensates for changes in test chamber fluid volume based on the calculated expansion or contraction of such fluid over the range of temperature and pressure profiles of a given test.

The leak-tolerant apparatus of the present invention is therefore disclosed for use in cooperation with an absolute fluid pressure sensor and comprises a housing having an interior portion defining a fluid fillable test chamber and an exterior portion. The apparatus further comprises a fluid-temperature sensor in thermal communication with the test chamber fluid and fluid-conditioning means in fluid communication with the test chamber for controlling the temperature of the fluid disposed therein in accordance with predetermined temperature profiles prescribed by the Federal Test Procedure. Still further, the apparatus comprises volume compensation means in fluid communication with the housing exterior portion for compensating for changes in test chamber fluid volume. Finally, the apparatus includes control means in electrical communication with the fluid temperature sensor, the fluid pressure sensor and the volume compensation means for determining the quantity of fluid required to be provided to or evacuated from the fluid compensation means in accordance with the Ideal Gas Law ($PV=nRT$).

In accordance with the invention, there is further disclosed a leak-tolerant method of controlling the volume of a test chamber filled with a fluid having a predetermined mass, volume, temperature and pressure time $t_0$ and used to measure evaporative emissions from motor vehicles in accordance with prescribed fluid temperature profiles. As disclosed, the method includes the steps of (1) measuring the temperature of the test chamber fluid at a selected time sample $t_n$ (where n is a positive integer); (2) measuring the absolute fluid pressure outside of the test chamber at the sample time $t_n$; (3) determining the volume of the test chamber fluid at sample time $t_n$ in accordance with the Ideal Gas Law (PV=nRT); (4) providing volume compensation means in fluid communication with the fluid outside of the test chamber for compensating for changes in the test chamber fluid volume; and (5) determining the volume of fluid required to be provided to or evacuated from the volume compensation means at time $t_n$.

In an alternative embodiment, there is further disclosed a similar leak-tolerant method of controlling the volume of a test chamber filled with a fluid having a predetermined mass, volume, temperature and pressure at a first selected sample time $t_{(n-y)}$ (where n is a positive integer) and used to measure evaporative emissions from motor vehicles in accordance with prescribed fluid-temperature profiles. As disclosed herein, the method of the alternative embodiment includes the steps of (1) measuring the temperature of the test chamber fluid at a second selected time sample $t_n$ (where y is a positive integer); (2) measuring the absolute fluid pressure outside of the test chamber at sample time $t_n$; (3) determining the volume of the test chamber fluid at sample time $t_n$ in accordance with the Ideal Gas Law (PV=nRT); (4) providing volume compensation means in fluid communication with the fluid outside of the test chamber for compensating for changes in the test chamber volume; and (5) determining the volume of fluid required to be provided to or evacuated from the volume compensation means at sample time $t_n$.

It should be noted that in the alternative method embodiment described above, step (5) further includes the steps of: (1) determining the rate at which fluid is provided to or evacuated from the volume compensation means in volume per unit time at $t_{(n-y)}$, (R1); (2) determining the rate at which fluid should be provided to or evacuated from the volume compensation means in volume per unit time at time $t_n$ (R2); (3) determining the difference between R1 and R2, ($R_d$); and (4) increasing or decreasing the rate at which fluid should be provided to or evacuated from the volume compensation means by $R_d$ so as to decrease or increase the volume of the test chamber accordingly.

The above objects and other objects, features, and advantages of the present invention are readily apparent from the following detailed description of the best mode for carrying out the invention when taken in connection with the accompanying drawings.

BEST MODES FOR CARRYING OUT THE INVENTION

Figure 1:
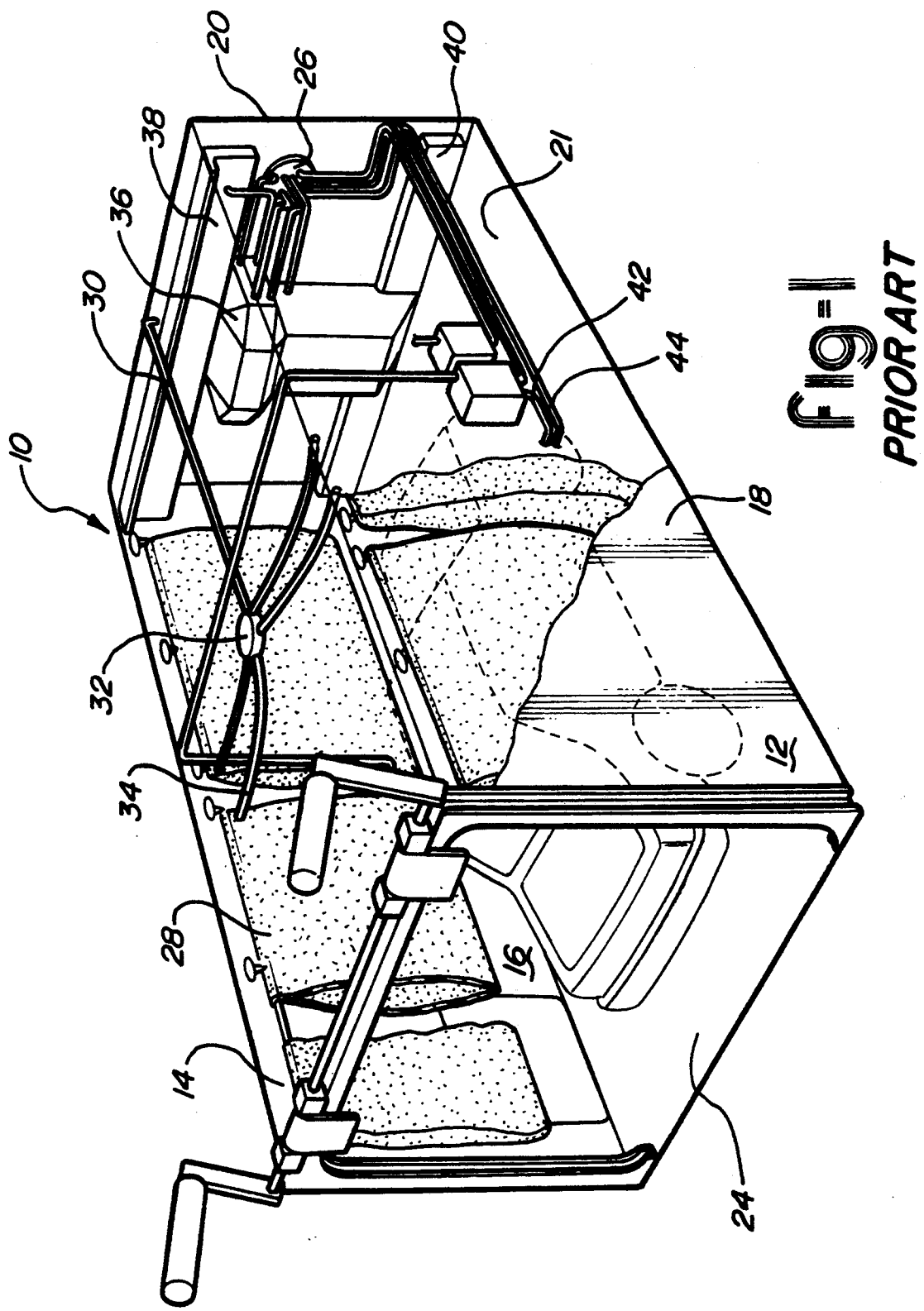
FIG. 1 is a perspective view of a prior art SHED.

Referring now to FIG. 1 of the drawings, a prior art variable-volume Sealed Housing For Evaporative Determination (SHED) is shown generally indicated by reference numeral 10. SHED 10 is a generally rectangular enclosure having a bottom portion 12, a top portion 14, side portions 16 and 18, and a rear portion 20. A vehicle entrance/exit door 22 is also provided to define a fluid-fillable test chamber 21. SHED 10 further includes an operator egress door 24 and a plurality of penetrations 26 for sample ports, temperature probes, and the like. Still further, prior art SHED 10 includes a plurality of air-expandable and partially air-filled bags 28 provided in fluid communication with an external pumping means (not shown) through tubing 30, manifold 32 and branch tubing 34.

Still referring to FIG. 1, there is shown Heating, Ventilating And Cooling means 36 in fluid communication with air supply plenum 38 and return air plenum 40. SHED 10 includes a pair of resistive temperature devices (RTDs), one of which is shown and designated by reference numeral 42. As indicated above, prior art SHED 10 utilizes a pure pressure feedback control system to determine the differential pressure between the test chamber fluid and the fluid outside of SHED 10. A sample probe 44 is also provided for extracting test chamber fluid to determine the mass of evaporative emissions such as hydrocarbon.

Figure 2:
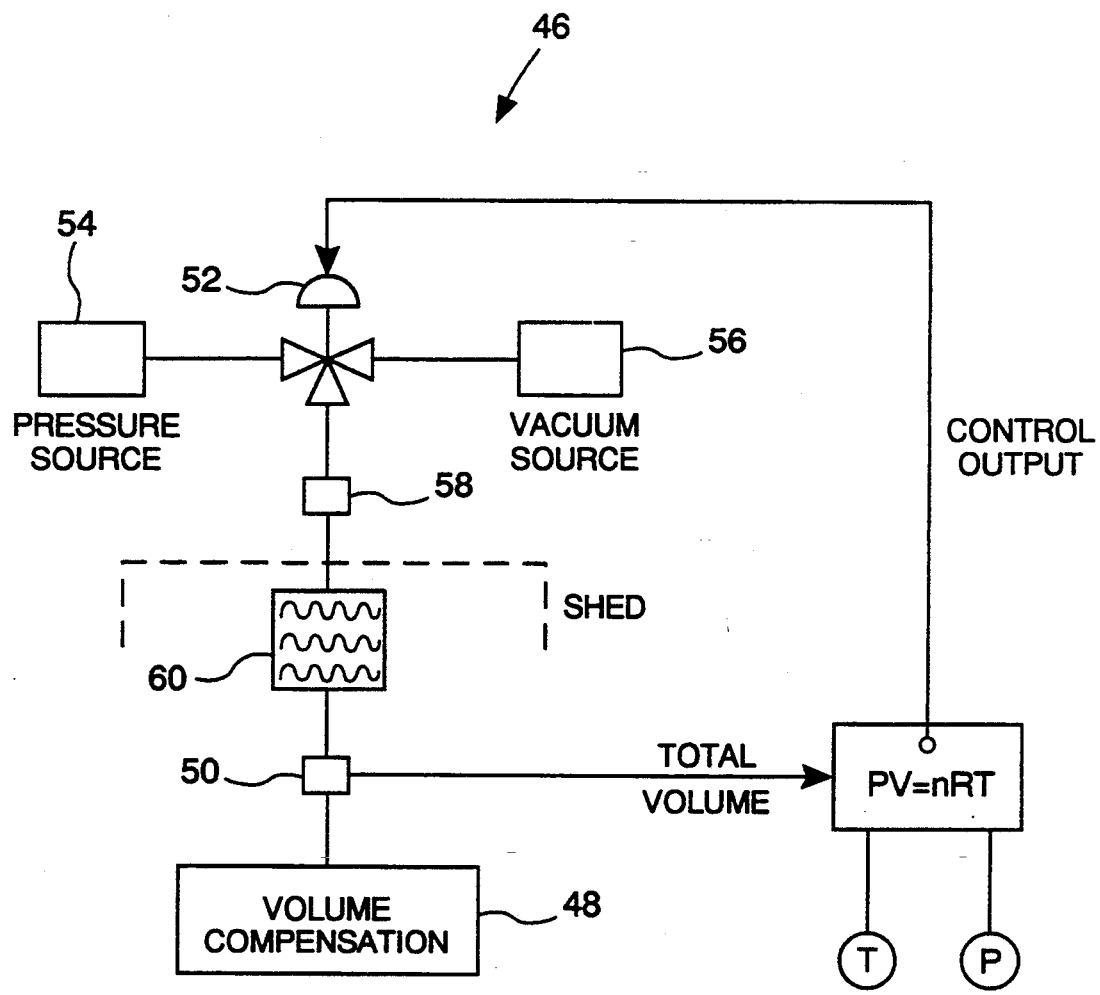
FIG. 2 is a schematic diagram of the open loop control system of the present invention.

Turning now to FIG. 2, there is shown a schematic diagram of the open loop control system of the present invention designated generally by reference numeral 46. As seen, control system 46 includes a volume compensation device 48 such as the prior art wall-mounted inflatable bags, a movable ceiling or other suitable volume compensating means as described more thoroughly below. Control system 46 further includes a flow metering device 50 for measuring the volume or mass of fluid (typically air) provided to or evacuated from volume compensation device 48 and a flow metering device such as control valve 52 for providing positive or negative volume compensation to volume compensation means 48. As shown in FIG. 2, pumps 54 and 56 or other suitable pumping means may be utilized to perform this function. Thus, in the preferred embodiment, pumps 54 and 56 may comprise one or more positive displacement pumps provided in fluid communication with a plurality of wall-mounted inflatable bags or a movable ceiling as described below. Still further, when the control system of the present invention is utilized with a fixed-volume test chamber, a filtered pump such as a zero-air pump may be provided as the positive volume compensation source so as to avoid the introduction of contaminants into the test chamber environment. In the preferred embodiment, control system 46 further includes a desiccant filter/dryer 58 for dehumidifying air provided to volume compensation device 48 as well as a heat exchanger 60 for stabilizing the temperature of fluid provided to volume compensation means 48.

Figure 3:
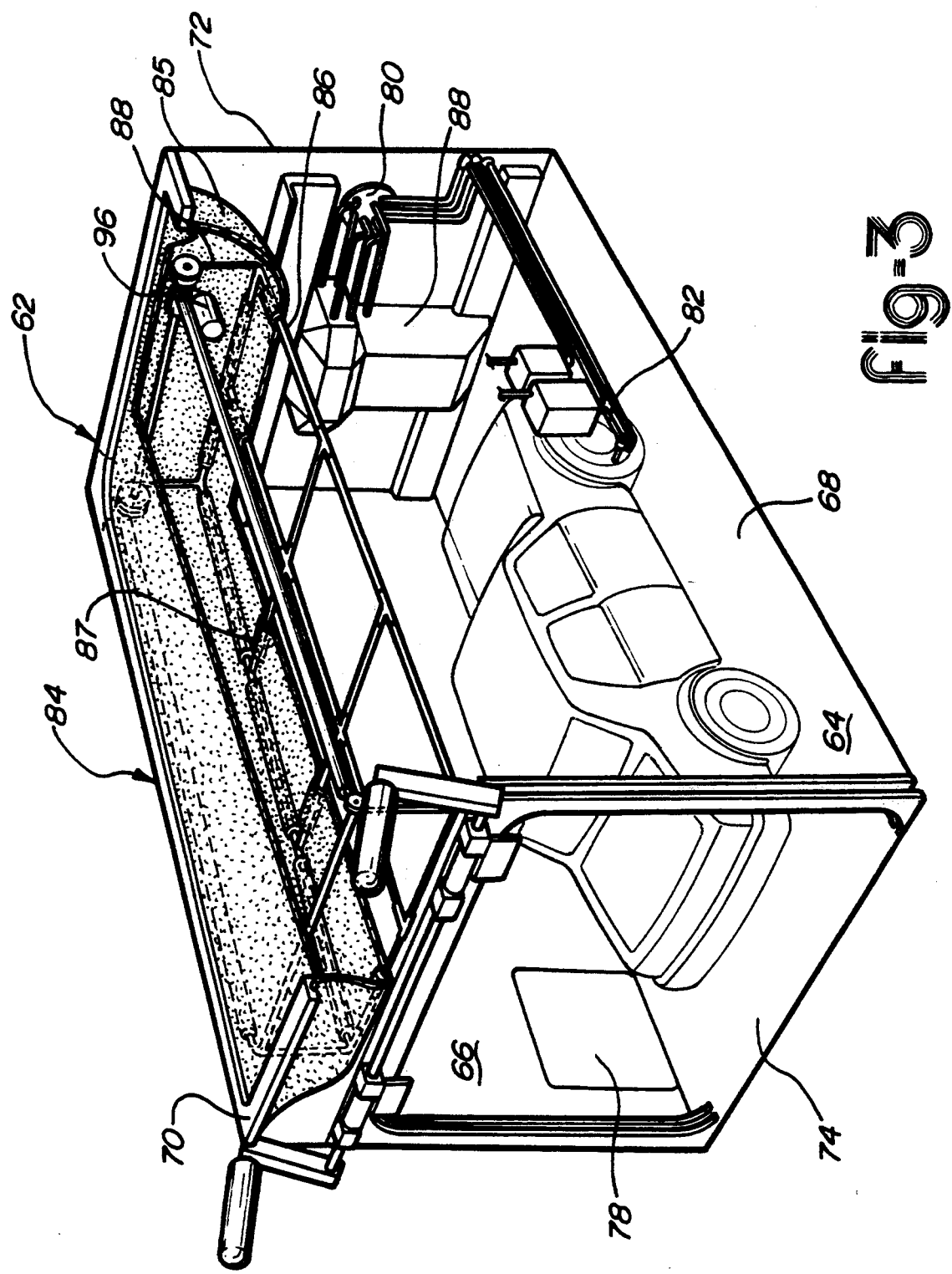
FIG. 3 is a perspective view of a typical SHED incorporating the control system of FIG. 2.

With reference now to FIG. 3, a sealed housing incorporating the control system of the present invention is shown generally designated by reference numeral 62. Like prior art SHED 10, SHED 62 is also preferably rectangular in shape and includes a bottom portion 64, side portions 66 and 68, top portion 70 and rear portion 72. SHED 62 further includes a vehicle entrance/exit door 74, an operator egress door 78 and a plurality of penetrations 80 which are provided for sample ports, temperature probes such as RTD 82, and the like. SHED 62 may include volume compensation means such as the wall-mounted, fluid-expandable bags as disclosed in the prior art and shown in FIG. 1. In a preferred embodiment as shown in FIG. 3, however, SHED 62 utilizes a volume compensation device 84 comprising a fluid-expandable and partially fluid-filled receptacle 85 which defines a movable ceiling. As shown in FIG. 3, receptacle 85 is made of a flexible material such as Tedlar ® which is adapted to be affixed in a sealed relationship with SHED top portion 70. Receptacle 85 is further provided in fluid communication with the fluid (typically air) outside of the SHED 62 and includes a substantially rigid frame 86 affixable to the receptacle upper inner surface by material straps 87 or other suitable attachment means. As seen, there is further provided engagement means such as electric motor 96 and linkage 88 for raising or lowering ceiling 85 in accordance with the control system of the present invention. SHED 62 further includes a heating, ventilating and cooling system (HVAC) 88 for conditioning the test chamber fluid in accordance with the prescribed temperature profiles of the Federal Test Procedure.

In a second preferred embodiment, SHED 62 may, in place of receptacle 85, utilize one or more flow metering devices such as a positive displacement pump as the volume compensation device. In operation, the volume of fluid required to be provided to or evacuated from the test chamber may be determined and controlled by the control system of the present invention in the same manner as described below.

The Control System

With reference to FIGS. 4–8, the preferred embodiments of the leak-tolerant control system of the present invention will now be described in detail. At the outset, it should be understood that the control system of the present invention has been designed based on the understanding that fluid of known mass, temperature, pressure and volume will expand and contract predictably in accordance with the Ideal Gas Law (PV-nRT). Thus, the control system of the present invention has been designed to compare the mass flow, volumetric flow, total mass or total volume of test chamber fluid present at selected sample times with the rate or total change in temperature so as to determine the amount of fluid which must be provided to or evacuated from the volume compensation device utilized.

In the preferred embodiments of FIGS. 4–7, the control system therefore comprises a feedback compared to a set point corresponding to the determined volume, mass or rate of fluid flow in volume or mass per unit time at a first selected sample time $t_n$, where n is a positive integer. This set point is compared with volume, temperature and pressure feedback from sample time $t_n$ and a previous selected sample time $t_{(n-y)}$, where y is a positive integer, through the use of a PID control loop so as to determine the required amount of fluid to be provided to or evacuated from the volume compensation means to avoid pressurization. This feedback is received from at least one temperature sensor which is in thermal communication with the test chamber fluid and preferably disposed therein and at least one pressure sensor disposed outside of the test chamber. In contrast to prior art control systems, the control system of the present invention does not utilize or require a differential pressure transducer.

Method Of Operation

Referring now to FIGS. 4–9, the method of operation of the control system of the present invention will be described in further detail.

Figure 4:
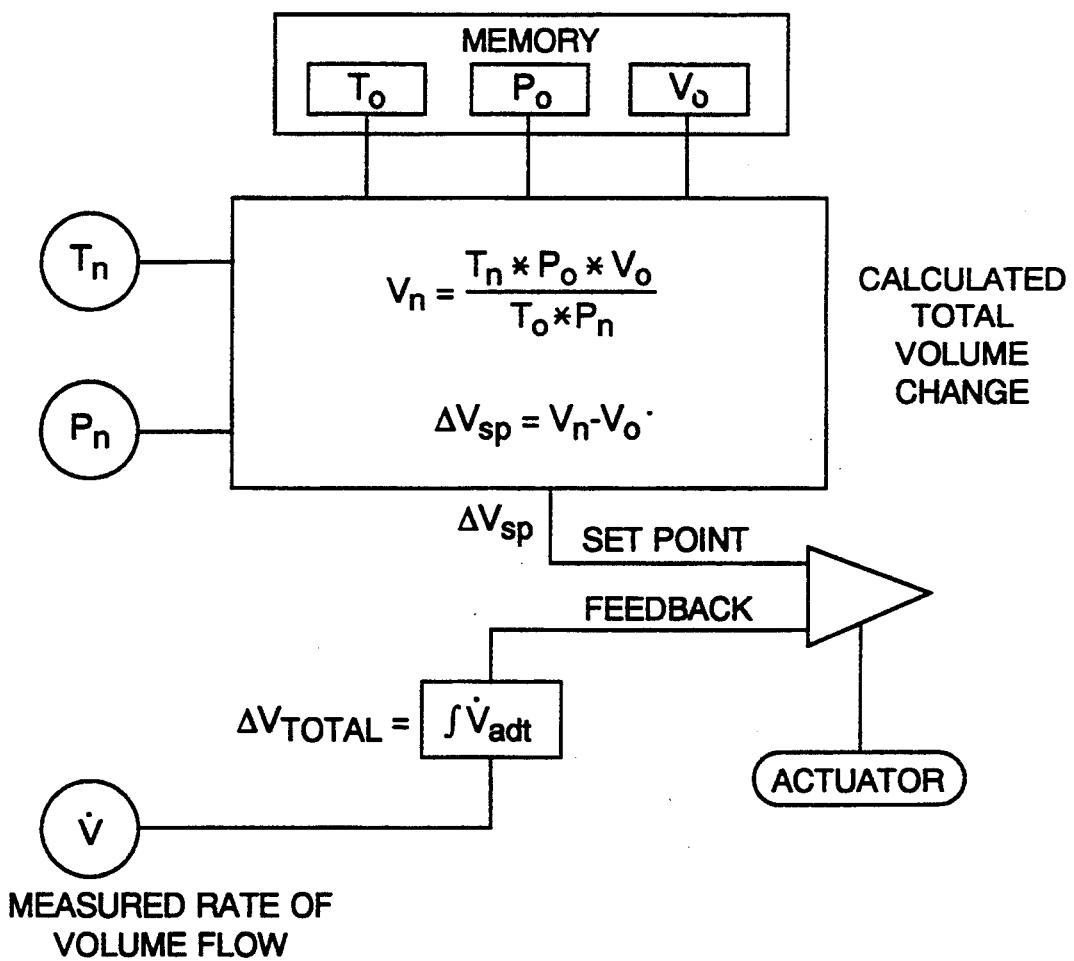
FIG. 4 is a schematic diagram of one preferred embodiment of the control system of the present invention.
Figure 5:
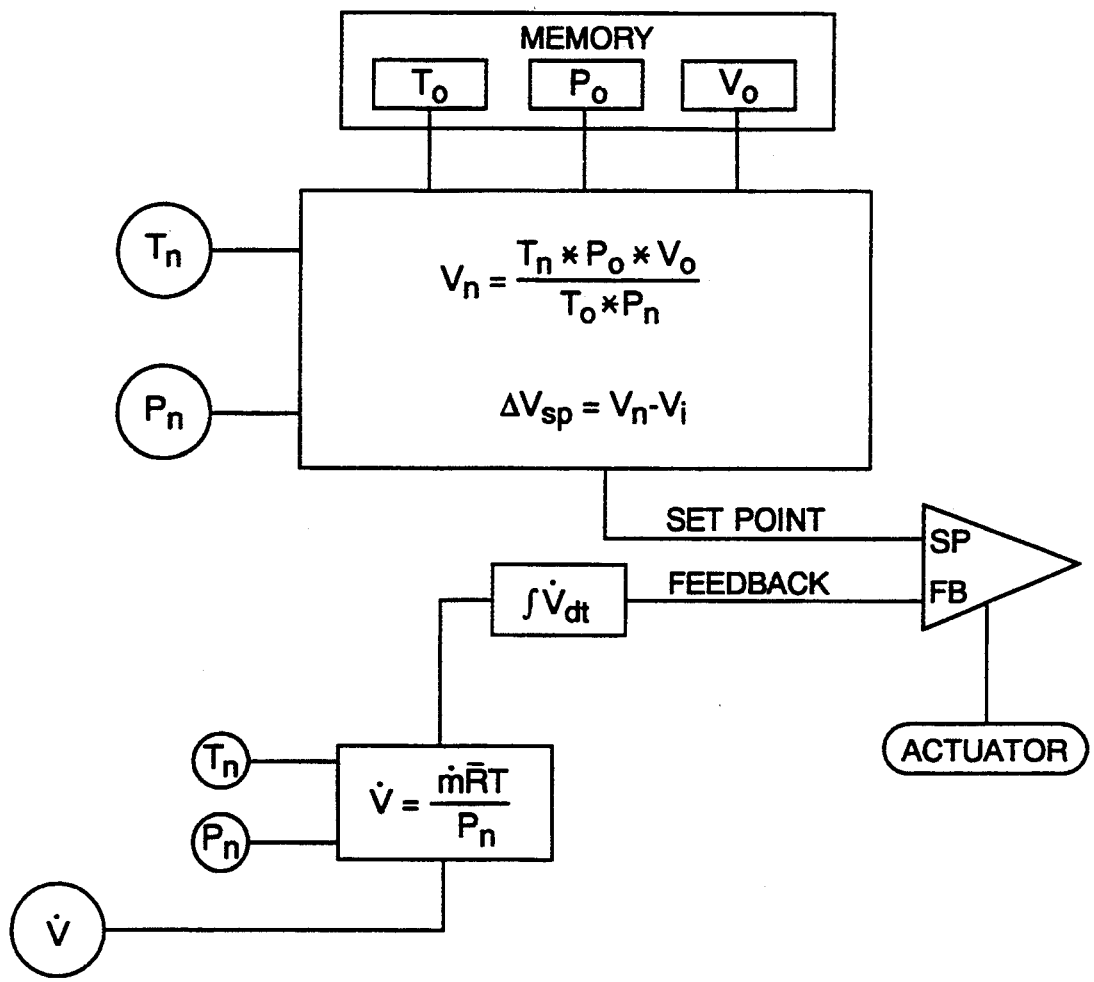
FIG. 5 is a schematic diagram of a second preferred embodiment of the control system of the present invention.

As shown in the schematics of FIGS. 4 and 5, a first preferred embodiment of the control system of the present invention includes the steps of comparing the total volume or mass of fluid present in the vehicle test chamber to the total change in temperature and pressure so as to predictively determine the required volume to be provided to or evacuated from the volume compensation means in accordance with the Ideal Gas Law (PV=nRT), where,
P=pressure,
V=volume,
n=molecular weight,
R=universal gas constant, and
T=temperature.

As those skilled in the art will recognize, between sample times $t_0$ and $t_n$, where n is a positive integer, the change in volume can be predictively determined in accordance with the formula:

$$\frac{P_0 V_0}{T_0} = \frac{P_n V_n}{T_n}.$$

Solving for $V_n$ yields:

$$V_n = \frac{T_n P_0 V_0}{T_0 P_n}$$

The change in test chamber fluid volume $V_n - V_o$ may be further designated $\Delta V_{sp}$. This value $\Delta V_{sp}$ may be provided as a set point in a PID control loop of a feedback control circuit wherein feedback is provided and compared to the determined total fluid volume which has been provided to or evacuated from the test chamber between sample times $t_o$ and $t_n$ ($\Delta V_{total}$). It should be noted that $\Delta V_{total}$ is measured through the use of a volumetric flow meter, the output of which is integrated over time. Once determined, this volume difference, ($V_d$), $\Delta V_{sp} - \Delta V_{total}$ may be provided to or evacuated from the volume compensation means so as to compensate for the decrease or increase in volume of the test chamber fluid.

With reference to FIG. 5, a second preferred embodiment of the control system of the present invention is disclosed wherein the step of determining the total volume of fluid which has been provided to or evacuated from the test chamber between times $t_0$ and $t_n$, ($\Delta V_{total}$) includes the initial step of measuring the mass flow of fluid which is being provided to or evacuated from the test chamber at time $t_n$, ($\dot{m}$). Utilizing an adaption of the Ideal Gas Law (PV=mRT), where $\bar{R}$ is the specific gas constant, this total mass may thereafter be converted to $\Delta V_{total}$. As those skilled in the art will recognize $$\bar{R} = R/M$$

where M is the molecular weight of the gas.

Figure 6:
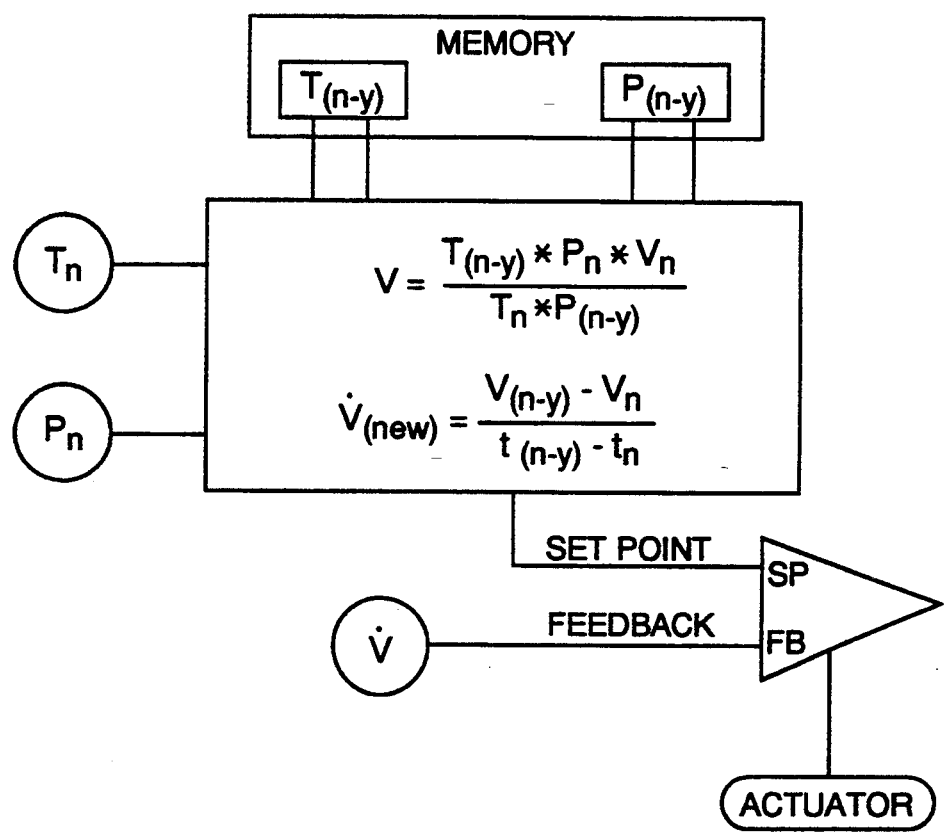
FIG. 6 is a schematic diagram of a third preferred embodiment of the control system of the present invention.

Referring now to FIG. 6, a third preferred embodiment of the control system of the present invention is disclosed which, instead of determining and comparing the total volume or mass of fluid provided to or evacuated from the volume compensation means, compares the volumetric or mass flow to the rate of temperature and pressure change. Like the control system of FIGS. 4 and 5, the third preferred embodiment also assumes that the mass, volume, temperature and pressure of the test chamber fluid has been measured or predetermined at a first selected sample time, here $t_{(n-y)}$, where n and y are both positive integers.

At a second selected sample time $t_n$, the temperature of the test chamber fluid and the absolute fluid pressure outside of the test chamber are measured. Again, provided with this information, the volume of the test chamber fluid at sample time $t_n$ ($V_{new}$) may be predictably determined in accordance with the Ideal Gas Law (PV=nRT). This volume, $V_{new}$, must then be compared to the determined volume of the test chamber fluid at sample time $t_n$ to determine the volume difference therebetween ($V_d$). Once determined, $V_d$ may be divided by the elapsed time between sample times $t_n$ and $t_{(n-y)}$. As those skilled in the art will recognize, this calculation will yield the determined rate at which fluid should be provided to or evacuated from the volume compensation means at sample time $t_n$ in volume per unit time. This value may then be compared to the determined rate at which fluid is provided to or evacuated from the volume compensation means at sample time $t_{(n-y)}$ (volume per unit time) to yield a determined rate difference $R_d$. By increasing or decreasing the rate of flow of fluid by $R_d$, the test chamber volume will be decreased or increased accordingly so as to avoid pressurization.

Figure 7:
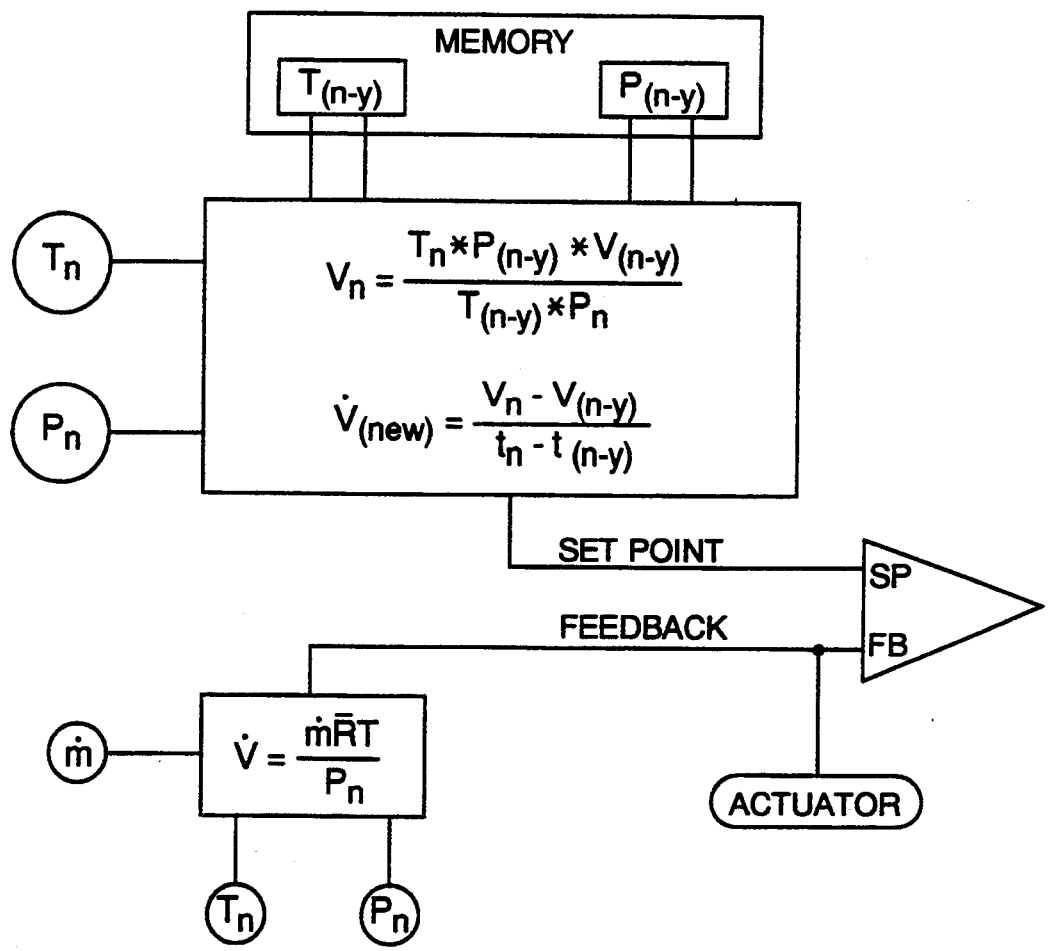
FIG. 7 is a schematic diagram of a fourth preferred embodiment of the control system of the present invention.
Figure 8:
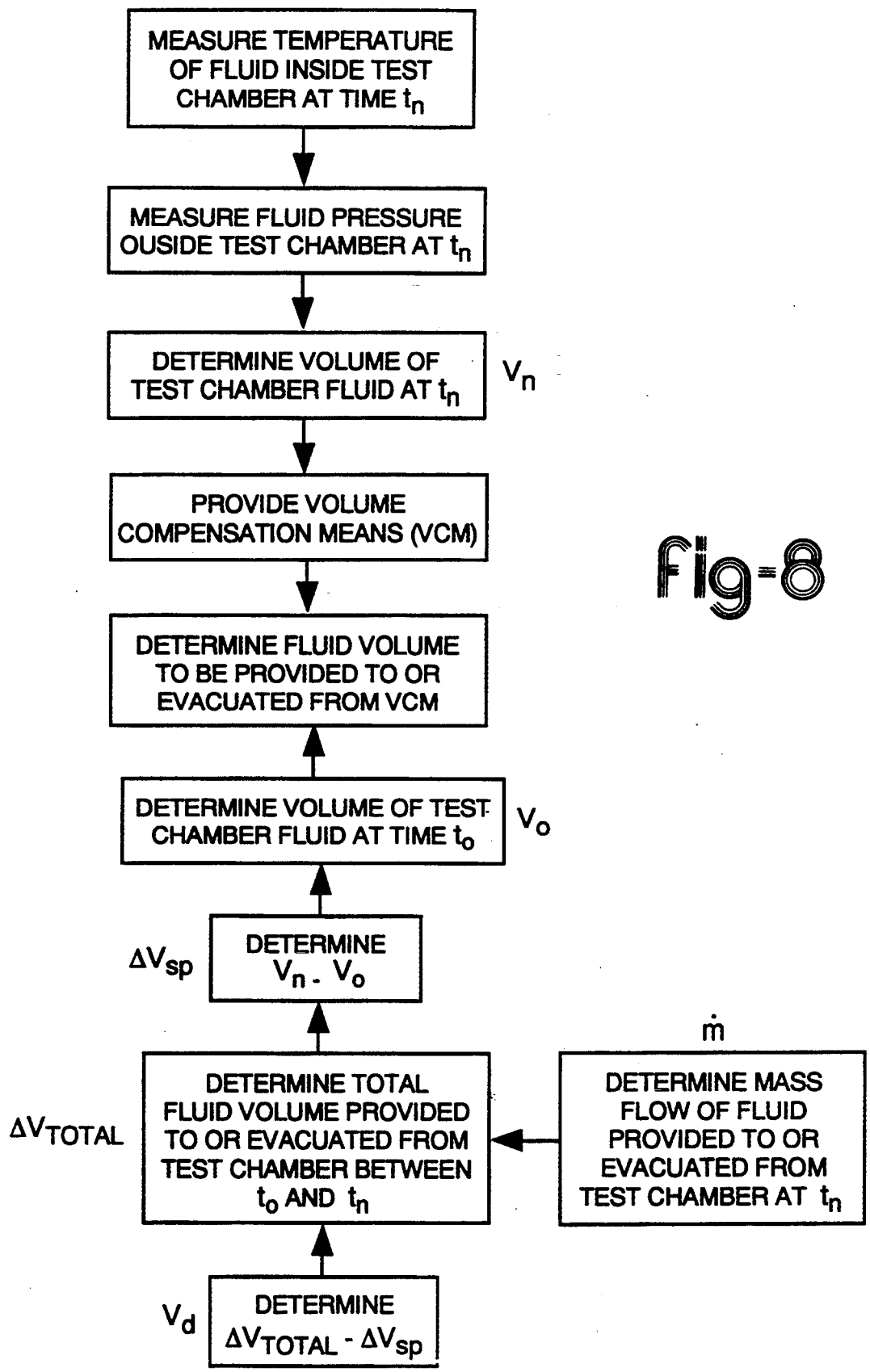
FIG. 8 is a block diagram illustrating the method steps of the present invention.
Figure 9:
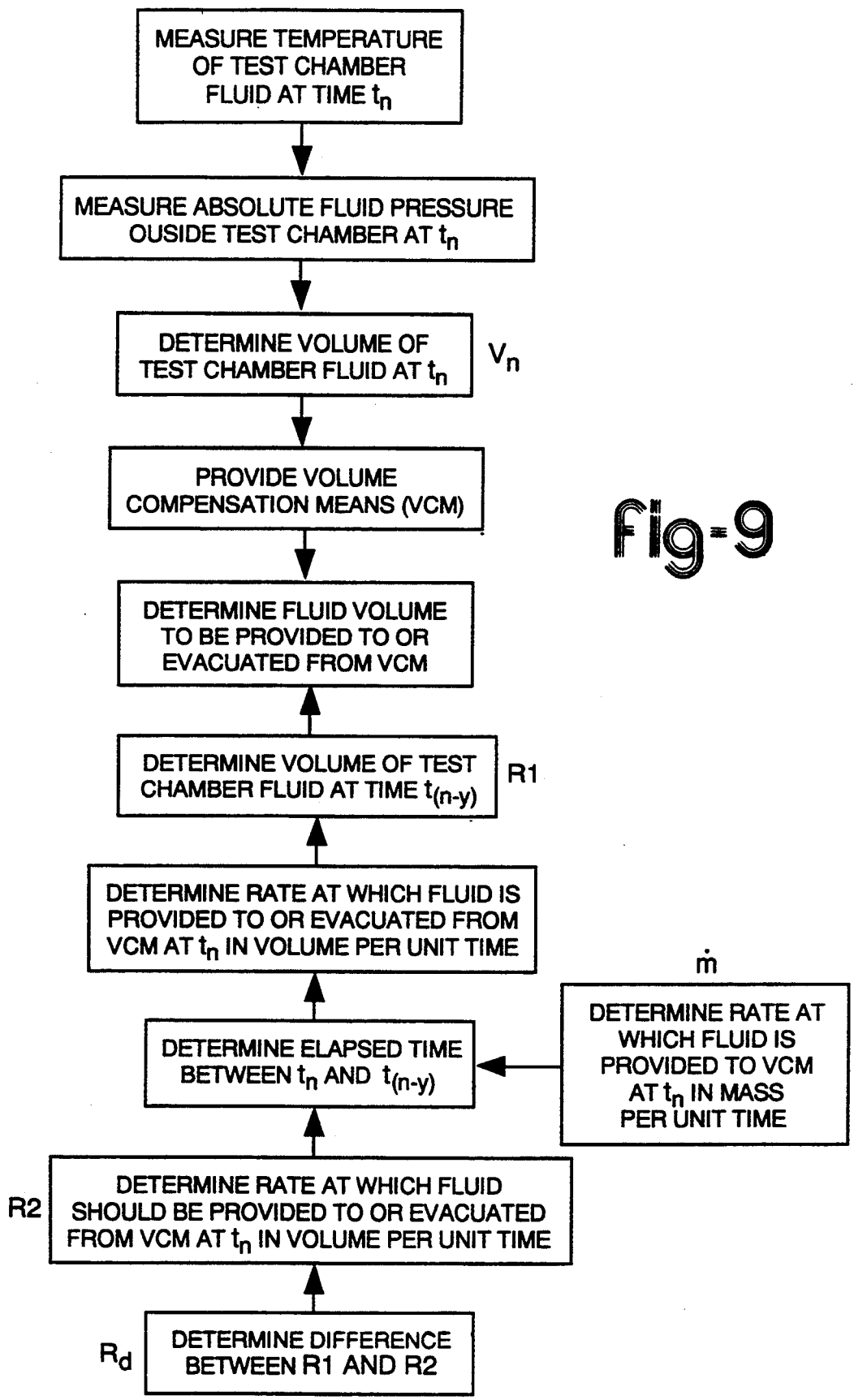
FIG. 9 is a block diagram illustrating the method steps of an alternative embodiment of the method of present invention.

In the fourth preferred embodiment of FIG. 7, it is seen that the step of determining the rate at which fluid is provided to or evacuated from volume compensation means at sample time $t_n$ further includes the step of determining the rate at which fluid is provided to the volume compensation means at sample time $t_n$ (in mass per unit time, $\dot{m}$). Once determined, this rate is converted to a corresponding rate in volume per unit time in accordance with an adaption of the Ideal Gas Law (PV=m$\bar{R}$T) as referenced above. The method steps of the present invention are also shown in block diagram format in FIGS. 8 and 9.

While the best modes for carrying out the present invention have been described in detail, those familiar with the art to which this invention relates will recognize various alternative designs and embodiments for practicing the invention as defined by the following claims.

What is claimed is:

1. A leak-tolerant apparatus for use in cooperation with an absolute fluid pressure sensor for measuring evaporative emissions from motor vehicles in accordance with prescribed fluid-temperature profiles, comprising:

a housing having an interior portion defining a fluid-fillable test chamber and an exterior portion;

a fluid-temperature sensor in thermal communication with said test chamber fluid;

fluid-conditioning means in fluid communication with said test chamber for controlling the temperature of said fluid disposed in said test chamber;

volume compensation means in fluid communication with said housing exterior portion for compensating for changes in said test chamber fluid volume; and control means in electrical communication with said fluid temperature sensor, said fluid pressure sensor and said volume compensation means for determining the quantity of fluid required to be provided to or evacuated from said volume compensation means in accordance with the Ideal Gas Law (PV=nRT).

2. An apparatus as in claim 1, wherein said volume compensation means comprises a flow metering device.

3. An apparatus as in claim 1, wherein said control means comprises a microprocessor.

4. An apparatus as in claim 1, wherein said control means comprises a feedback control circuit.

5. An apparatus as in claim 4, wherein said control means includes a PID control loop.

6. A leak-tolerant apparatus for use in cooperation with a barometric air pressure sensor for measuring evaporative hydrocarbon emissions from motor vehicles in accordance with prescribed air-temperature profiles, comprising:

a housing having an interior portion defining an air-fillable test chamber and an exterior portion;

an air-temperature sensor disposed in said test chamber;

air-conditioning means in fluid communication with said test chamber for controlling the temperature of said air disposed in said test chamber;

volume compensation means in fluid communication with said housing exterior portion for compensating for changes in said test chamber fluid volume; and control means in electrical communication with said air temperature sensor, said air pressure sensor and said volume compensation means for determining the quantity of air required to be provided to or evacuated from said volume compensation means in accordance with the Ideal Gas Law (PV=nRT) so as to compensate for changes is said test chamber air volume.

7. A leak-tolerant method of controlling the volume of a test chamber filled with a fluid having a predetermined mass, volume, temperature and pressure at time $t_o$ and used to measure evaporative emissions from motor vehicles in accordance with prescribed fluid-temperature profiles, the method comprising the steps of:

measuring the temperature of said test chamber fluid at a selected sample time $t_n$, where n is a positive integer;

measuring the absolute fluid pressure outside of said test chamber at said sample time $t_n$;

determining the volume of said test chamber fluid at said sample time $t_n$ in accordance with the Ideal Gas Law (PV=nRT);

providing volume compensation means in fluid communication with said fluid outside of said test chamber for compensating for changes in said test chamber fluid volume; and determining the volume of fluid required to be provided to or evacuated from said volume compensation means at time $t_n$.

8. The method of claim 7, wherein the step of determining the volume of fluid required to be provided to or evacuated from said volume compensation means includes the steps of:

determining the difference between said test chamber fluid volume at said times $t_o$ and $t_n$, ($\Delta V_{sp}$);

determining the total volume of fluid which has been provided to or evacuated from said test chamber between said times $t_o$ and $t_n$, ($\Delta V_{total}$);

determining the difference between $\Delta V_{sp}$ and $\Delta V_{total}$ ($V_d$); and providing or evacuating fluid having volume $V_d$ to or from said volume compensation means so as to compensate for changes in fluid volume in said test chamber accordingly.

9. The method of claim 8, wherein the step of determining $V_{total}$ includes the steps of:

determining the mass flow of fluid being provided to or evacuated from said test chamber at time $t_n$, ($\dot{m}$); and converting $\dot{m}$ to $\Delta V_{total}$ in accordance with an adaption of the Ideal Gas Law ($PV = m\bar{R}T$).

10. A leak-tolerant method of controlling the volume of a test chamber filled with a fluid having a predetermined mass, temperature and pressure at a first selected sample time $t_{(n-y)}$, (where n and y are both positive integers) and used to measure evaporative emissions from motor vehicles in accordance with prescribed fluid-temperature profiles, the method comprising the steps of:

measuring the temperature of said test chamber fluid at a second selected sample time $t_n$;

measuring the absolute fluid pressure outside of said test chamber at said sample time $t_n$;

determining the volume of said test chamber fluid at said sample time $t_n$ in accordance with the Ideal Gas Law ($PV = nRT$);

providing volume compensation means in fluid communication with said fluid outside of said test chamber for compensating for changes in said test chamber fluid volume; and determining the volume of fluid required to be provided to or evacuated from said volume compensation means at said sample time $t_n$.

11. The method of claim 10, wherein the step of determining the volume of fluid required to be provided to or evacuated from said volume compensation means at said sample time $t_n$ includes the steps of:

determining the difference between said test chamber fluid volume at said sample times $t_n$ and $t_{(n-y)}$;

determining the elapsed time between said sample times $t_n$ and $t_{(n-y)}$;

determining the rate at which fluid is provided to or evacuated from said volume compensation means at said sample time $t_n$ in volume per unit time, (R1);

determining the rate at which fluid should be provided to or evacuated from said volume compensation means at said sample time $t_n$ in volume per unit time, (R2);

determining the difference between R1 and R2, ($R_d$);

increasing or decreasing the rate at which fluid is provided to or evacuated from said volume compensation means by $R_d$ to decrease or increase the volume of said test chamber accordingly.

12. The method of claim 11, wherein said step of determining the rate at which fluid is provided to or evacuated from said volume compensation means at said sample time $t_n$ includes the steps of:

determining the rate at which fluid is provided to said volume compensation means at said sample time $t_n$ in mass per unit time; and converting said determined rate in mass per unit time to a corresponding rate in volume per unit time in accordance with the Ideal Gas Law ($PV = m\bar{R}T$).

* * * * *